United States Patent [19]
Froggatt

[11] Patent Number: 5,841,032
[45] Date of Patent: Nov. 24, 1998

[54] VARIABLE AND FIXED FREQUENCY PULSED PHASE LOCKED LOOP

[75] Inventor: Mark E. Froggatt, Yorktown, Va.

[73] Assignee: The United States of America as represented by the Administrator National Aeronautics and Space Administration, Washington, D.C.

[21] Appl. No.: 792,909

[22] Filed: Jan. 24, 1997

Related U.S. Application Data

[60] Provisional application No. 60/013,216, Feb. 2, 1996.

[51] Int. Cl.⁶ .................................................... G01N 29/18

[52] U.S. Cl. .................................. 73/597; 73/609; 73/610

[58] Field of Search .............................. 73/597, 609, 761, 73/862.27, 862.29, 862.31; 367/125, DIG. 2

[56] References Cited

U.S. PATENT DOCUMENTS

| | | |
|---|---|---|
| 4,363,242 | 12/1982 | Heyman . |
| 4,624,142 | 11/1986 | Heyman . |
| 5,150,620 | 9/1992 | Allison . |
| 5,237,516 | 8/1993 | Heyman . |
| 5,404,753 | 4/1995 | Froggatt ..................................... 73/1 B |

*Primary Examiner*—Ronald L. Biegel
*Attorney, Agent, or Firm*—Robin W. Edwards

[57] ABSTRACT

A measuring apparatus uses a variable and fixed frequency pulsed phase locked loop to measure the phase shift caused by a delay path to a high degree of accuracy. This accurate measurement of total phase change through greater than 360 degrees allows the apparatus to measure strain in bolts or other materials. The apparatus is able to identify features on a waveform through pattern recognition, and measure untracked phase differences with better reliability than simple thresholding techniques permit.

19 Claims, 10 Drawing Sheets

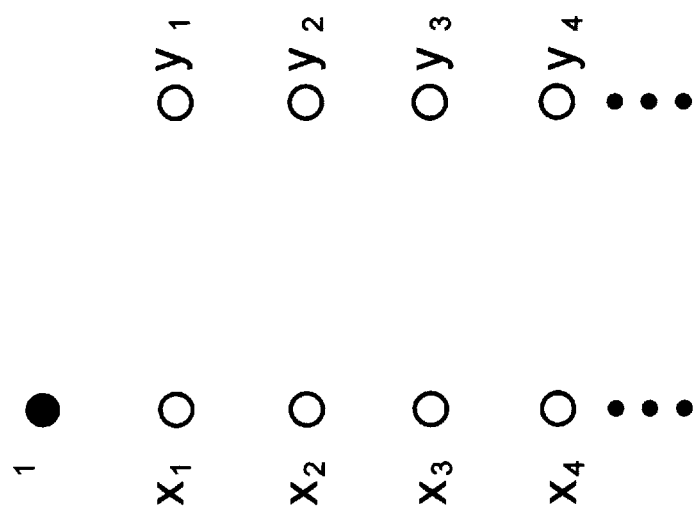

$$\begin{bmatrix} a & b & c & d \\ b & a & b & c \\ c & O & a & b \\ O & O & O & a \end{bmatrix}$$

LINEAR CORRELATION

FIG. 7

$$\begin{bmatrix} a & b & c & d \\ d & a & b & c \\ c & d & a & b \\ b & c & d & a \end{bmatrix}$$

CIRCULAR CORRELATION

FIG. 6 bolts or other materials.
VARIABLE AND FIXED FREQUENCY PULSED PHASE LOCKED LOOP This application claims the benefit of U.S. Provisional application Ser. No. 60/013,216, filed Feb. 2, 1996.

CROSS REFERENCE TO RELATED APPLICATIONS

This application is related to U.S. Pat. No. 5,237,516, issued Aug. 17, 1993, U.S. Pat. No. 5,150,620, issued Sep. 29, 1992, and U.S. Pat. No. 5,404,743, issued Apr. 11, 1995, the specifications of which are hereby incorporated by reference.

ORIGIN OF THE INVENTION

The invention described herein was made by an employee of the United States Government and may be manufactured and used by the government for governmental purposes without the payment of any royalties thereon or therefor.

BACKGROUND OF THE INVENTION

1. Field of the Invention

This invention relates generally to measuring and testing, and more specifically, to a variable or fixed frequency pulsed phase locked loop measuring apparatus.

2. Description of the Related Art

A need exists to characterize states of metals and other materials and systems, for example, by measuring pressure derivatives of ultrasound phase velocities to determine combinations of third-order elastic constants, or by measuring stress derivatives in materials, or other quantities which undergo changes in ultrasonic phase velocities as a function of some thermodynamic variable or variables.

There are three different ways to obtain phase/delay measurements. The first is the use of time of flight instruments. These instruments use a pulse to excite a transducer. The received echo then trips a threshold. The time between excitation and the tripping of the threshold is the measurement.

Current time of flight systems are limited in resolution by the clocking speed of the counters used to measure the time of flight. Time of flight systems are also subject to any changes in amplitude that may cause the threshold to be tripped by a different part of the returning echo. Pulses are broadband signals that form a broad beam, and suffer from dispersion in most materials.

The second method of measuring phase is the use of variable frequency pulsed phase locked loops. Two examples of a pulsed phase locked loop are described in U.S. Pat. Nos. 4,363,242 and 4,624,142, which are both issued to Heyman and assigned to the National Aeronautics and Space Administration (NASA) and are both incorporated into this application by reference.

In U.S. Pat. No. 4,363,242, the radio frequency output of a voltage controlled oscillator (VCO) is periodically gated to a transducer which produces acoustic waves in a bolt. The reflected acoustic waves are converted to electrical signals by the transducer and gated to a mixer. The mixer also receives the output from the VCO and produces an output which is filtered by a low pass filter. The output of the low pass filter is a DC signal proportional to the phase difference change from a fixed phase difference between the two input signals to the mixer. The DC signal is then sampled at an instance and held by a circuit in response to a "P" signal (from a sample hold). The output of the circuit is integrated and then applied to the VCO to change the frequency of the VCO such that the phase difference between the two inputs to the mixer remains at the fixed phase difference. The frequency of the VCO is thus a measure of the change in strain of the bolt.

In U.S. Pat. No. 4,624,142, a double reference pulse phase locked loop measures the phase shift between the burst signals initially derived from the same periodic signal source, which is also a VCO, and delayed by different amounts because of two different paths. A first path is from a transducer to a front surface of the sample and back, and a second path is from the transducer to the rear surface of the sample and back. A first pulse phase locked loop including a phase detector and phase shifter forces the tone burst signals delayed by the second path in phase quadrature with the periodic signal source. A second pulse phase locked loop including another phase detector forces the tone burst signals delayed by the first path into phase quadrature with the phase shifted periodic signal source.

Current variable frequency methods have two problems. The first problem is that current timing methods do not allow the sample point to be shifted by increments smaller than one period. This prevents the instrument from acquiring information about many of the return echo's characteristics. The second problem is that because it is variable frequency, the measurements of delay are generally only valid for small changes in frequency. While this is not a problem in strain measurements where the percentage change of the path is small, it prevents the instrument from being used to track surfaces where the percentage change in path length can exceed 50%.

The third method of measuring phase is the use of fixed frequency pulsed phase locked loops. One example of a fixed frequency pulsed phase locked loop is described in U.S. Pat. No. 5,214,955 issued to Yost et al. and assigned to NASA. These instruments also gate a tone burst to the transducer, then mix the received signal back to baseband. The phase of the reference signal is then changed to force the sampled baseband signal to zero, thus locking the system at quadrature. The phase shift is accomplished by a calibrated electronically controlled phase shifter.

One problem with the current fixed frequency system is the limited phase shift available from the electronically controlled phase shifter. A second problem is the timing. Since all of the timing is generated from one clock, either the transmission gating or the receive sampling must be asynchronous. If the total change in path length exceeds the length of the tone burst, the sampling of the phase will no longer be on the received tone burst, and the system will fail.

SUMMARY OF THE INVENTION

An object of the present invention is to provide an accurate measurement of total phase change through greater than 360 degrees to allow the apparatus to measure strain in bolts or other materials.

Another object of the invention is to provide a variable or fixed frequency pulse phase locked loop which can track surfaces of irregular specimens undergoing ultrasonic inspection.

Another object of the present invention is to provide a variable or fixed frequency pulse phase locked loop which is able to identify features on a wave form through pattern recognition algorithms, and measure untracked phase differences with better reliability than simple thresholding techniques permit.

Another object of the present invention is to provide a variable or fixed frequency pulse phase locked loop which uses numerically controlled oscillators in an ultrasonic or fiber optic environment to allow precise control of phase and frequency, and eliminate the need to measure phase and frequency.

Another object of the present invention is to provide a variable or fixed frequency pulse phase locked loop which uses two independent counters driven by separate numerically controlled oscillators, allowing precise setting of the sample point or receive gate in increments smaller than one period.

Another object of the present invention is to provide a variable or fixed frequency pulse phase locked loop that allows a very broad band of operating frequencies, from 0 to 15 MHZ.

Another object of the present invention is to provide a variable or fixed frequency pulse phase locked loop which uses a computer to close the pulsed phase locked loop, thus allowing more sophisticated locking algorithms to be used.

Another object of the present invention is to provide a variable or fixed frequency pulse phase locked loop which digitizes waveforms at high interleaved sampling rates, such as 2 GHz.

These and other objects of the invention are met by providing an apparatus which uses a variable and fixed frequency phase locked loop to measure phase shift in a sample caused by a delay path. The device generates a signal from a numerically controlled oscillator, converts the signal to pulses, then uses the pulses to gate a tone burst to a transducer. When the tone burst ends, the output of the transducer returns to a high impedance state. The receiver amplifies the return echos from reflections in the sample. These amplified echos are then converted into a digital signal which is sent to a personal computer. The personal computer is used to compare the phase of the signal generated by the return echos with the phase of the transmitted signal. A computer program adjusts the phase or the frequency of the numerically controlled oscillators so that the phase difference between the two signals is zero, thus locking the system in phase. A pattern recognition algorithm is used by the computer to identify features on the waveform generated by the return echos.

These and other features and advantages of the measuring apparatus of the present invention will become more apparent with reference to the following detailed description and drawings.

BRIEF DESCRIPTION OF THE DRAWINGS

A more complete appreciation of the invention and the many of the attendant advantages thereof will be readily obtained as the same becomes better understood by reference to the following detailed description when considered in connection with the accompanying drawings, wherein:

FIG. 5 shows the vector arrays.

FIG. 6 is a circular correlation matrix.

FIG. 7 is a linear correlation matrix.

DETAILED DESCRIPTION OF THE INVENTION

Figure 1:
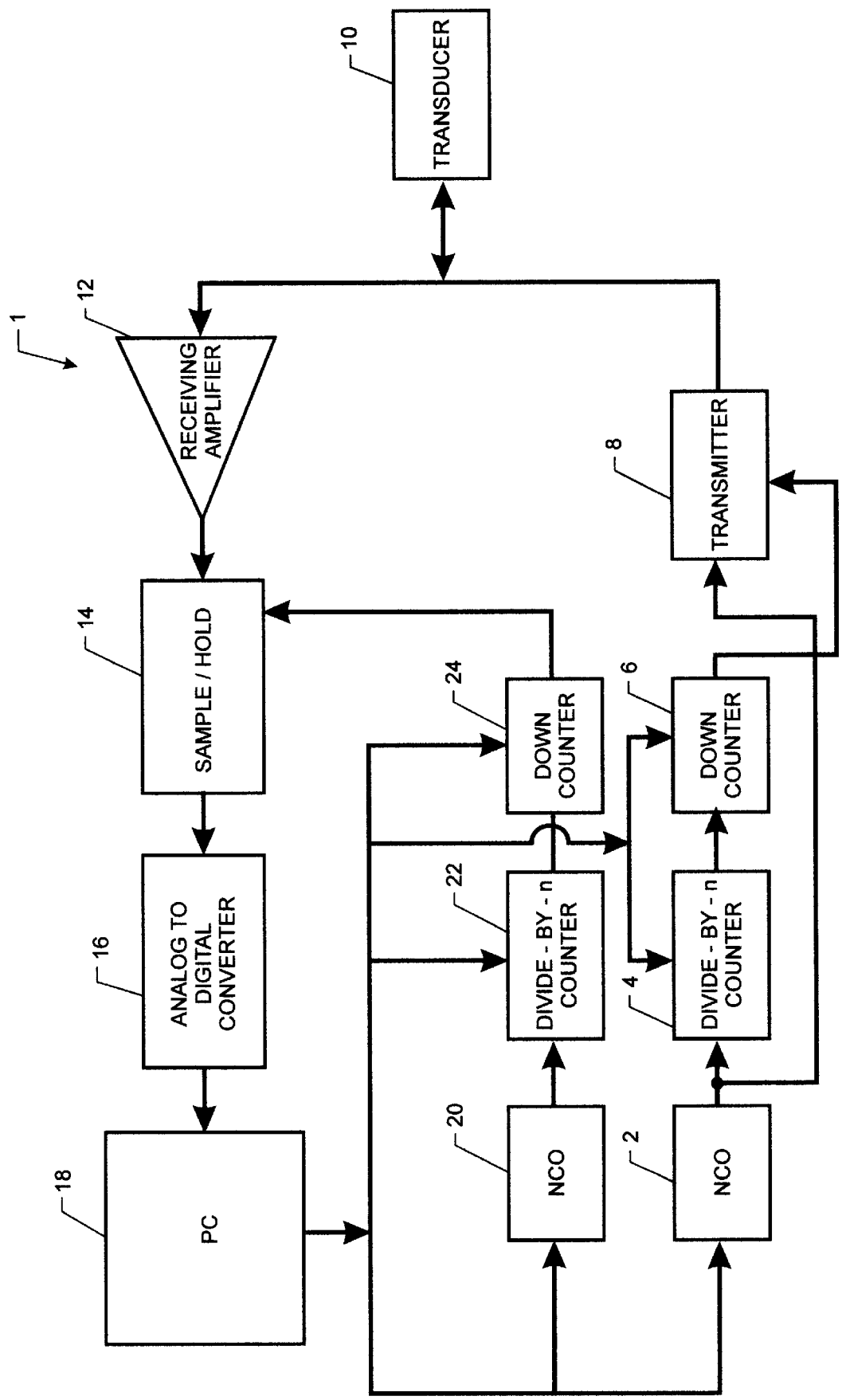
FIG. 1 shows a block diagram of the present invention.
Figure 2:
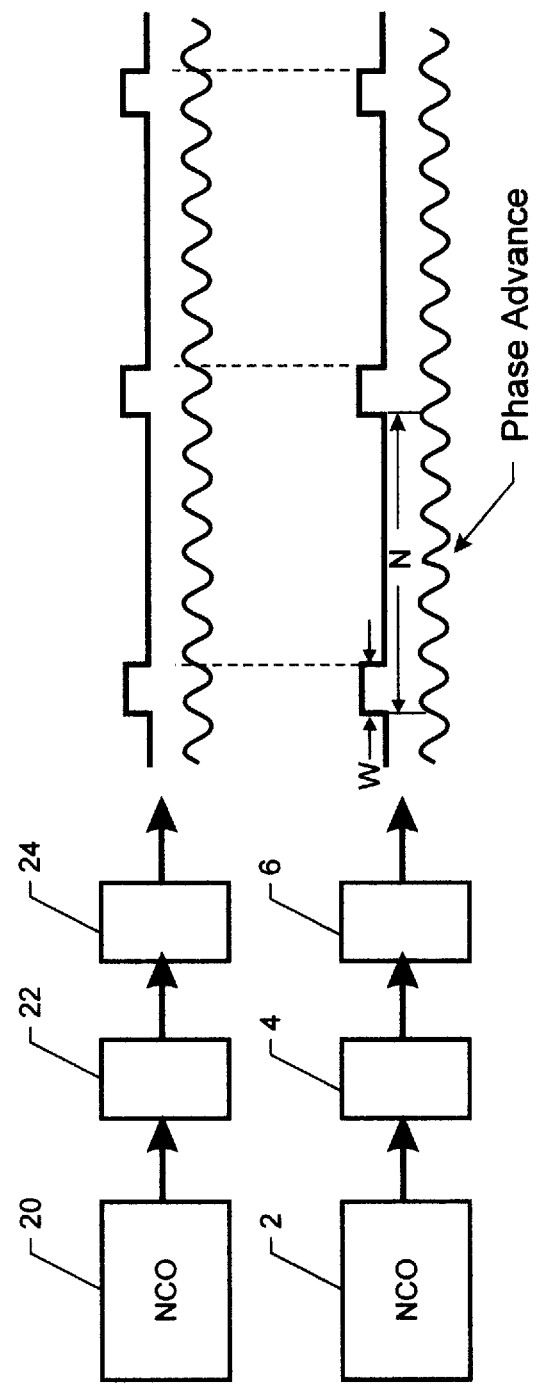
FIG. 2 shows the phase advance produced by the numerically controlled oscillator.

Referring now to FIG. 1, a variable or fixed frequency pulsed phase locked loop is generally referred to by the numeral 1, and includes two numerically controlled oscillators (NCOs) 2 and 20. The output of NCO 2 drives the divide by N counter 4 and down counter 6. The NCO 2 generates a signal and sends it to a divide by N counter 4, which uses this signal as a clock and counts to determine the timing of its outputs. These divide by N pulses trigger a down counter 6. The frequency and phase of the NCO 2 output determines the frequency and phase of the clock signal used by divide by N counter 4 and down counter 6. The frequency of the clock is equal to the frequency of the NCO 2. The counters 4 and 6 can be programmed by the host personal computer (PC) 18 to change the width (in number of cycles) and frequency (also in number of cycles) of the output pulse. As shown in FIG. 2, this counter circuitry produces an output that is high for a programmable number of clock periods W and repeats every N clock periods where N is also programmable.

The pulse from counters 4 and 6 is used to gate the analog signal from NCO 2. It should be noted that the gating signal from counters 4 and 6 always remains synchronous with the analog signal being gated, and always maintains the same phase relative to the analog signal being gated.

The pulses are sent to a transmitter 8 which converts the pulses into a tone burst. The sample time with respect to the transmitted tone burst is determined by changing the phase of the signal driving the divide by N counter 4. The tone burst is applied to the specimen via transducer 10 which is affixed to the specimen. Echos from the tone burst are detected by transducer 10 and converted into an electrical signal. The receiving amplifier 12 then amplifies the electrical signal.

A receive pulse is generated by a second NCO 20 which drives a second divide by N counter 22 and a second programmable down counter 24. Divide by N counter 22 can be programmed by the PC 18 to set the frequency of the receive pulse. The down counter 24 can be programmed by the PC 18 to set the width of the receive pulse. The receive pulse can be used to drive a sample and hold circuit 14 for the received electrical signal, or gate the input to an analog correlator. The output of the sample and hold or the analog correlator can then be digitized using a relatively slow analog to digital (A/D) converter 16.

If the two NCO's 2 and 20 operate at the same frequency and phase, which is not difficult to achieve with NCO's, and the counters for each are simultaneously reset, then the outputs of the counters will be identical, and their rising edges will occur at exactly the same time. If the phase of NCO 2 is delayed (by briefly lowering the frequency or by directly changing the phase with the PC 18), then all of the edges in counters' 4 and 6 output will be delayed with respect to counters 22 and 24. This delay is cumulative and has no limit. By increasing the frequency of NCO 2 or advancing its phase, the edges can similarly be moved in opposite direction. Using NCO's, all of this can be done precisely. The total delay of the output pulse from counters 4 and 6 with respect to counters 22 and 24 is the signed sum of the phase advances made by NCO 2 and 20. Since the pulses are separated by a fixed angle, changing the phase or frequency will change the separation in time of the two pulses from counters 22 and 24 and counters 4 and 6, as shown in FIG. 2.

Phase lock is accomplished by programming the PC 18 to change the phase and frequency of the NCOs 2 and 20 such that the output of the A/D converter 16 is zero. The PC 18 allows the user to implement more sophisticated methods of finding a lock point than would be feasible in a completely analog system. Receiving amplifier 12 increases the size (amplitude) of the signal. Sample-hold amplifier 14 has an output equal to whatever the value of the signal on its output was when the output from divide by N counter 22 and down counter 24 went from low to high. Analog to digital converter 16 converts the voltage at its input to a digital word that can be interpreted by the PC 18. The role of sample-hold amplifier 14 and analog to digital converter 16 is then to communicate to the PC 18 what the value of the received signal was when the output from divide by N counter 22 and down counter 24 went from high to low.

The frequency of either NCO 2 or 20 is changed by the PC 18 to determine whether the phase change is greater than 180 degrees. The PC 18 then changes the phase of the NCO 2 or 20 to measure the total phase shift of the received signal through 360 degrees.

Figure 3:
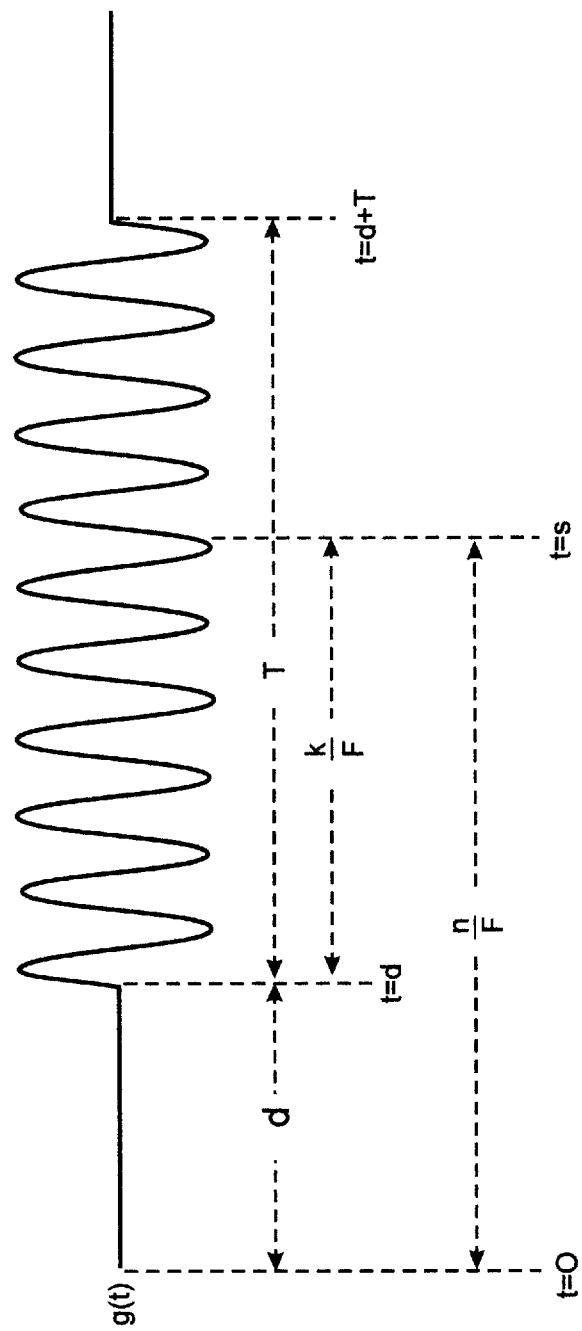
FIG. 3 shows a time line representing the time history of a received tone burst employed by the present invention.

Ideally, the delay between the transmitted and received tone bursts can be determined by the equation $$\Phi = 2\pi dF \quad (1)$$

where $\Phi$ is the phase delay of the signal, d is the time delay of the signal, and F is the frequency of the signal. However, the system must sample the signal at some time within the delayed tone burst as shown in FIG. 3. This requires an additional operating phase delay $$\Phi = 2\pi dF + 2\pi(k/F) \quad (2)$$

where k and d are operating unknowns. In FIG. 3, n is equal to $\Phi/(2\pi)$, where $\Phi$ is equal to the phase shift in radians. Therefore, two lock points $\Phi(1)$ and $\Phi(2)$ $$\Phi(1) = 2\pi dF(1) + 2\pi(k/F(1)) \quad (3)$$

$$\Phi(2) = 2\pi dF(2) + 2\pi(k/F(2)) \quad (4)$$

are needed to record two phases and two frequencies in order to generate the two linear equations needed to find d and k.

These values are determined as follows. The received signal is used by the PC 18 to lock the system. The frequency and phase of this lock point are recorded as F(1) and $\Phi(1)$. The phase is advanced by $\Phi(2)$, and the frequency is then advanced by $2\pi F/\Phi(2)$. The system is then locked again, and the new frequency and phase are recorded as F(2) and $\Phi(2)$.

These values are then used in the following equation, which is derived in detail in U.S. Pat. No. 5,404,743:

$$k = (F(1)n(2) - (F(2)n(1)))/(F(1) - F(2)) \quad (5)$$

where $n(2) = \Phi(2)/(2\pi)$ and $n(1) = \Phi(1)/(2\pi)$.

The value of k is calculated and stored in the PC 18. This value is used to determine where in the tone burst the system has locked. However, using a change in frequency alone to calculate the delay is not an accurate method of measuring the delay, because the delay changes with changes in frequency.

Therefore, phase change must be used to measure the delay. This is done by changing the frequency such that less than a full cycle of phase shift is produced, that is, less than $\pi F/(4\Phi)$. The phase is then adjusted to lock the system. This process is repeated until F has been returned to its original value. The delay is then calculated from this change in the phase using equation (2).

Figure 4:
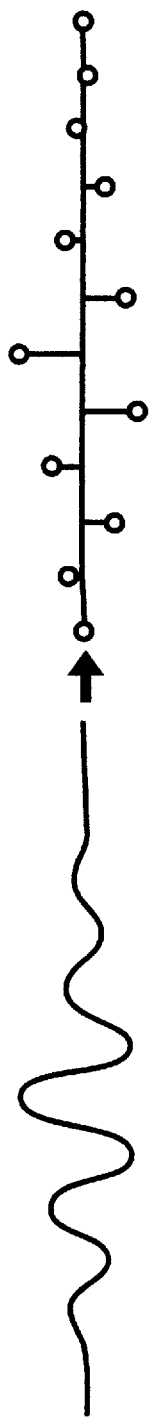
FIG. 4 is a graph of peak values from a waveform.

Alternatively, the sampled waveform can be analyzed by a neural network to determine how much it has shifted with respect to the reference signal. Processing the entire waveform is not necessary since the waveform is a relatively narrow band. Only the envelope of the waveform is processed by extracting the peak values as shown in FIG. 4. This set of peaks is then normalized to a maximum absolute value.

Only an integer shift can be detected. Although methods for locating local zero crossings and peaks are well known, a method for assessing how the zero crossings or peaks of one waveform relate to the zero crossings or peaks of a reference waveform must be used.

The system is implemented as a one-layer back propagation network, as shown in FIG. 5. If there is no shift with respect to the reference, the middle element of the y-vector is maximum. If there is a shift in x, this will be reflected by the same shift in y.

The network is trainable from a single data set. When this set is applied, the desired y vector is 1 at the neuron representing no shift, and 0 at all others. Logistic functions are used on the outputs. Training is normally completed in 100 to 1000 repetitions.

Shift invariance does not need to be learned by the network, because it can be imposed on the network by placing proper constraints on the network. The primary constraint is making the elements on a diagonal of the matrix equal, as shown in FIGS. 6 and 7. The bias level on each output neuron must also be equal. The matrix multiplication is carried out as a correlation.

Updates for the weights are carried out by computing the update for each weight in a diagonal and changing all of the weights by the average of these updates. In order to produce a complete linear correlation (from zero overlap to zero overlap), an output layer of twice the number of input neurons is used.

Figure 9:
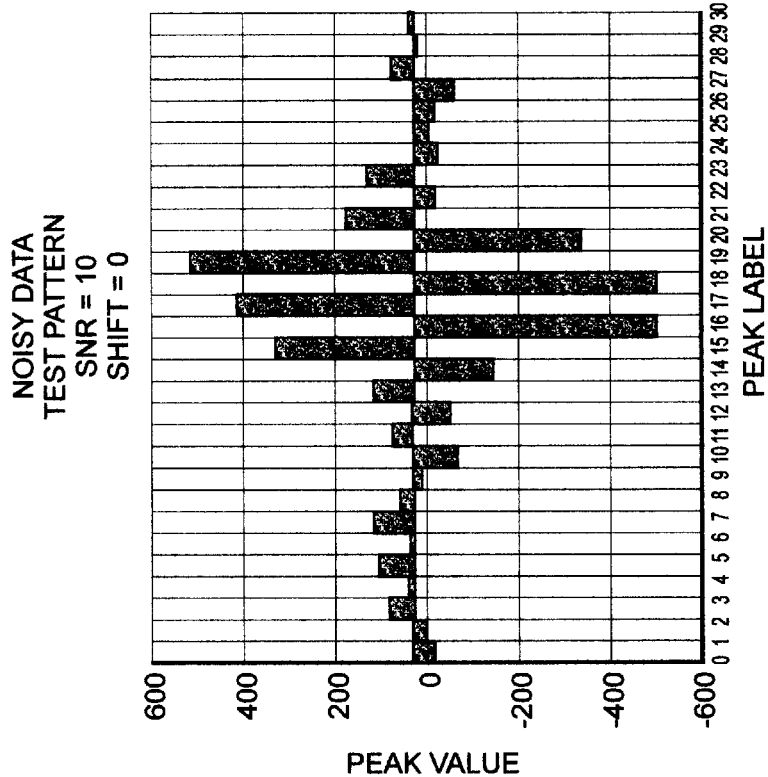
FIG. 9 is an example of a noisy received signal.
Figure 8:
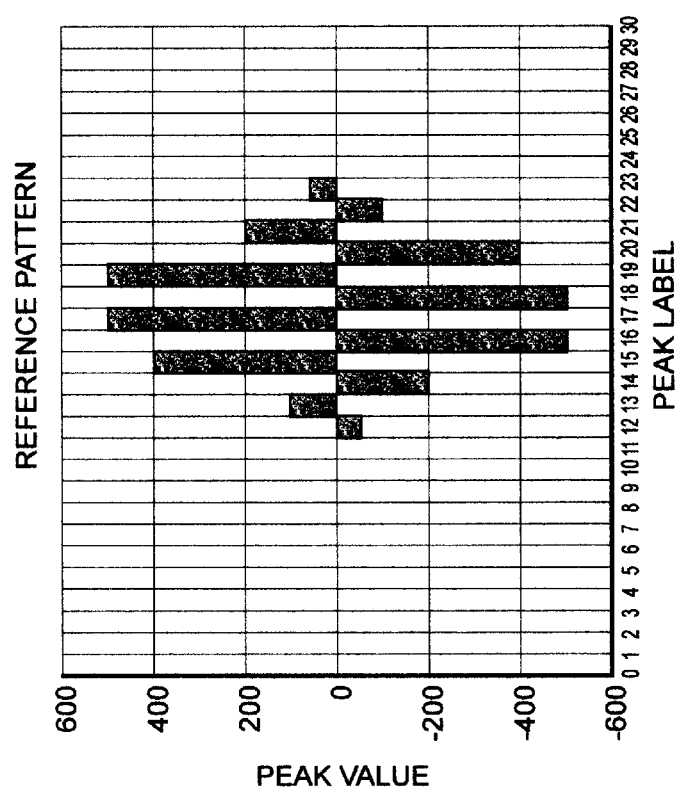
FIG. 8 is the reference signal.
Figure 11:
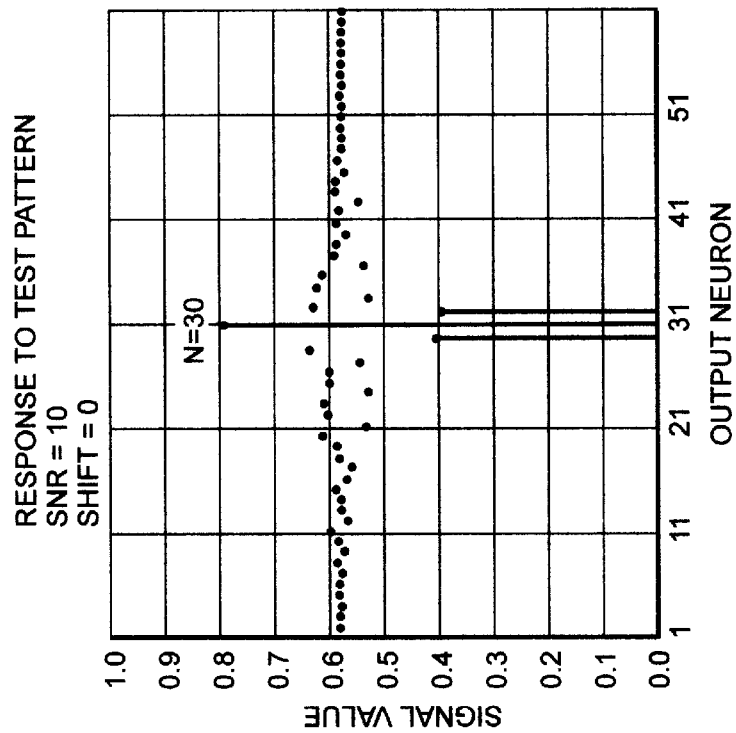
FIG. 11 is the network response to the received signal.
Figure 10:
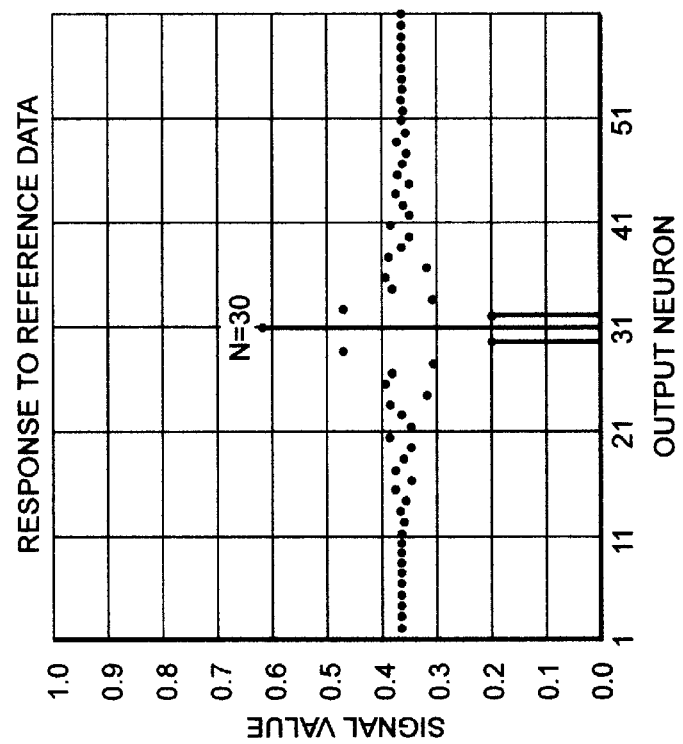
FIG. 10 is the network response to reference data.

The network is trained using an input set of noise free peaks. The input vector is N elements long with the remaining elements set equal to zero, as shown in FIG. 8. FIGS. 9 through 11 show that the response patterns to a noisy signal are relatively immune to noise. This network retains the fundamental characteristics of neural networks, such as weighted sums, updated weights, and generalization, yet it is simple enough to use in semi real time systems.

Figure 12:
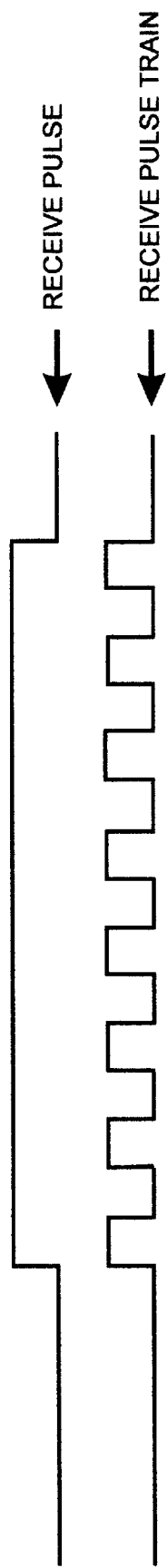
FIG. 12 shows the receive pulse replaced by a received pulse train.

In an alternative embodiment, the receive pulse is replaced by a receive pulse train as shown in FIG. 12. The individual pulses are then used to drive a high speed A/D converter. The data can be stored to produce a fully digitized waveform in only a few repetitions of the tone burst, or the data can be summed in a high speed digital accumulator to produce a more accurate phase signal.

Figure 13:
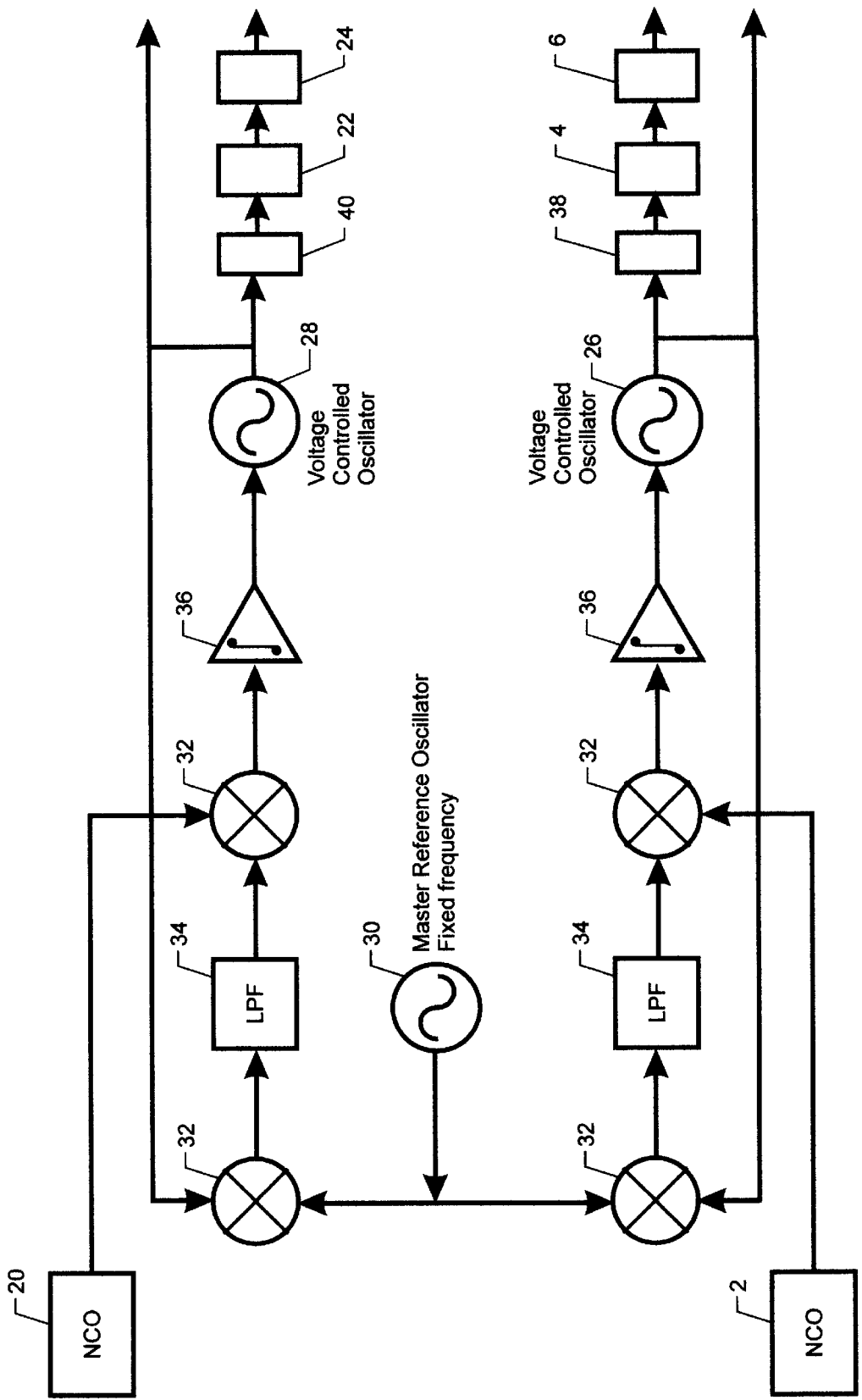
FIG. 13 is a block diagram of the present invention with high frequency voltage controlled oscillators.

In another embodiment, two high frequency voltage controlled oscillators (VCOs) 26 and 28 are phase locked to the NCOs 2 and 20 and a fixed reference frequency 30 as shown in FIG. 13. The mixers 32, low pass filters 34 and integrators 36 comprise the phase locked loop. The outputs of the VCOs 26 and 28 will be offset by the same phase offset as the NCOs 2 and 20. Prescalers 38 and 40 can then be used at the input to the counters 4 and 22 to reduce the VCO's 26 and 28 carrier frequency to a frequency at which readily available programmable TTL counters can operate. This creates a very high frequency pulsed phase locked loop.

Such loops, as shown in FIG. 13, can be used in modulated, open laser systems to track surfaces in the same manner as the ultrasonic system. Such loops can also be used in modulated, fiber optic laser systems to measure strain in optical fiber in much the same way as the ultrasonic system does in bolts.

Numerous modifications and adaptations of the present invention will be apparent to those skilled in the art. Thus, the following claims and their equivalents are intended to cover all such modifications and adaptations which fall within the true spirit and scope of the present invention.

What is claimed is:

1. An apparatus for measuring phase shift in a sample comprising the following interconnected elements:

first signal means for generating a first electrical signal;

second signal means for generating a second electrical signal;

first pulse means for generating first pulses that are synchronized to said first electrical signal;

second pulse means for generating second pulses that are synchronized to said second electrical signal;

gating means for gating said first electrical signal based on said first pulses;

first conversion means for converting said gated signal into a radiated wave;

transmitting means for transmitting said radiated wave onto a sample;

receiving means for receiving said radiated wave from said sample;

second conversion means for converting said received radiated wave into a third electrical signal;

sampling means for sampling said third electrical signal at a time determined by said second pulses, wherein the sample point is determined by the accumulated phase differences between said first electrical signal and said second electrical signal;

third conversion means for converting said sampled signal into a digital signal; and means for digitally varying the frequency and phase of said first and second electrical signals as desired such that said digital signal is zero.

2. An apparatus according to claim 1, further comprising means for pattern recognition to identify features on said third electrical signal.

3. An apparatus according to claim 1, further comprising means for amplifying said third electrical signal prior to sampling.

4. An apparatus according to claim 1, wherein said first signal means is a first numerically controlled oscillator.

5. An apparatus according to claim 1, wherein said second signal means is a second numerically controlled oscillator.

6. An apparatus according to claim 1, wherein said first pulse means is a first 8 bit programmable down counter triggered by a first 15 bit programmable divide by N counter.

7. An apparatus according to claim 1, wherein said second pulse means is a second 8 bit programmable down counter triggered by a second 15 bit programmable divide by N counter.

8. An apparatus according to claim 1, wherein said gating means and said first conversion means is a single gated transmitter with switchable output impedance.

9. An apparatus according to claim 1, wherein said transmitting means, said receiving means, and said second conversion means is a single transducer affixed to said sample.

10. An apparatus according to claim 1, wherein said sampling means is a sample/hold circuit.

11. An apparatus according to claim 1, wherein said third conversion means is an analog to digital converter.

12. An apparatus according to claim 1, wherein said means for digitally varying said first and second electrical signals is a computer programmed with an algorithm to change the phase and frequency of said first and second electrical signals such that the output of the analog to digital converter is zero.

13. An apparatus according to claim 1, wherein said means for digitally varying said first and second electrical signals is a computer programmed with an algorithm to change the phase of said first and second electrical signals such that the output of the analog to digital converter is zero.

14. An apparatus according to claim 1, wherein said means for digitally varying said first and second electrical signals is a computer programmed with an algorithm to change the frequency of said first and second electrical signals such that the output of the analog to digital converter is zero.

15. An apparatus according to claim 2, wherein said means for pattern recognition is a neural network computer program.

16. An apparatus according to claim 1, further comprising first and second high frequency voltage controlled oscillators phase locked to corresponding said first and second signal means and a fixed reference frequency.

17. An apparatus according to claim 16, further comprising a first prescaler between said first high frequency voltage controlled oscillator and said first pulse means and a second prescaler between said second high frequency voltage controlled oscillator and said second pulse means.

18. A method for measuring phase shift in a sample, comprising;

generating a first electrical signal;

generating a second electrical signal;

generating first pulses that are synchronized to said first electrical signal;

generating second pulses that are synchronized to said second electrical signal;

gating said first electrical signal based on said first pulses;

converting said gated signal into a radiated wave;

transmitting said radiated wave onto a sample;

receiving said radiated wave from said sample;

converting said received radiated wave into a third electrical signal;

sampling said third electrical signal at a time determined by said second pulses, wherein the sample point is determined by the accumulated phase differences between said first electrical signal and said second electrical signal;

converting said sampled signal into a digital signal; and digitally varying the frequency and phase of said first and second electrical signals as desired such that said digital signal is zero.

19. A method according to claim 18, further comprising the step of analyzing said third electrical signal with a pattern recognition algorithm to identify features of said third electrical signal.

* * * * *